(12) United States Patent
Bake et al.

(10) Patent No.: US 10,555,815 B2
(45) Date of Patent: *Feb. 11, 2020

(54) SURGICAL KIT FOR CARTILAGE REPAIR COMPRISING IMPLANT AND A SET OF TOOLS

(71) Applicant: EPISURF IP-MANAGEMENT AB, Stockholm (SE)

(72) Inventors: Nina Bake, Lidingö (SE); Richard Lilliestråle, Stockholm (SE); Manuel Otero Quevedo, Stockholm (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/324,351

(22) PCT Filed: Jul. 9, 2015

(86) PCT No.: PCT/EP2015/065781
§ 371 (c)(1),
(2) Date: Jan. 6, 2017

(87) PCT Pub. No.: WO2016/005542
PCT Pub. Date: Jan. 14, 2016

(65) Prior Publication Data
US 2017/0172747 A1    Jun. 22, 2017

(30) Foreign Application Priority Data
Jul. 9, 2014   (WO) ................. PCT/EP2014/064749

(51) Int. Cl.
*A61F 2/30*    (2006.01)
*A61B 17/00*   (2006.01)
*A61F 2/38*    (2006.01)

(52) U.S. Cl.
CPC .......... *A61F 2/30942* (2013.01); *A61B 17/00* (2013.01); *A61F 2/30756* (2013.01);
(Continued)

(58) Field of Classification Search
CPC .... A61F 2/30942; A61F 2/38; A61F 2/30756; A61F 2002/30878; A61F 2002/30952;
(Continued)

(56) References Cited

U.S. PATENT DOCUMENTS 4,180,910 A  1/1980 Straumann et al.
4,197,645 A  4/1980 Scheicher
(Continued)

FOREIGN PATENT DOCUMENTS

CN     102083374 A    6/2011
EP     1 698 307 A1   9/2006
(Continued)

OTHER PUBLICATIONS

Extended European Search Report dated Jun. 13, 2017 in European Patent Application No. 17155242.5.
(Continued)

*Primary Examiner* — Ajay Ojha
(74) *Attorney, Agent, or Firm* — Drinker Biddle & Reath LLP

(57) ABSTRACT

Embodiments herein relate to design methods for design of an individually customized implant, based on a 3D virtual model of an implant. The design method comprises identifying a damage area, presenting a virtual 3D view of said identified damage area, creating a 3D virtual implant comprising virtually placing in said 3D view a shape, wherein the area of the shape covers or partly covers said identified damage area, producing an implant based on said created 3D virtual implant.

18 Claims, 9 Drawing Sheets

(52) U.S. Cl.
CPC ........ *A61F 2/38* (2013.01); *A61F 2002/3013* (2013.01); *A61F 2002/30897* (2013.01); *A61F 2002/30948* (2013.01); *A61F 2002/30952* (2013.01)

(58) Field of Classification Search
CPC .... A61F 2002/3013; A61F 2002/30897; A61F 2002/30948
See application file for complete search history.

(56) References Cited

U.S. PATENT DOCUMENTS

| | | | |
|---|---|---|---|
| 4,964,865 A | 10/1990 | Burkhead et al. | |
| 5,520,692 A | 5/1996 | Ferrante | |
| 5,658,305 A | 8/1997 | Baker | |
| 5,716,360 A | 2/1998 | Baldwin et al. | |
| 5,743,916 A | 4/1998 | Greenberg et al. | |
| 5,976,147 A | 11/1999 | LaSalle et al. | |
| 6,063,091 A | 5/2000 | Lombardo et al. | |
| 6,165,177 A | 12/2000 | Wilson et al. | |
| 6,251,143 B1 | 6/2001 | Schwartz et al. | |
| 6,306,142 B1 | 10/2001 | Johanson et al. | |
| 6,520,964 B2 | 2/2003 | Tallarida et al. | |
| 6,799,066 B2 | 9/2004 | Steines et al. | |
| 7,658,879 B2 | 2/2010 | Solar | |
| 7,713,305 B2 | 5/2010 | Ek | |
| 7,824,181 B2 | 11/2010 | Sers | |
| 7,867,234 B2 | 1/2011 | Collazo | |
| 7,981,122 B2 | 7/2011 | Labadie et al. | |
| 8,062,302 B2 | 11/2011 | Lang et al. | |
| 8,066,708 B2 | 11/2011 | Lang et al. | |
| 8,083,745 B2 | 12/2011 | Lang et al. | |
| 8,105,330 B2 | 1/2012 | Fitz et al. | |
| 8,460,304 B2 | 6/2013 | Fitz et al. | |
| 8,641,721 B2 | 2/2014 | Aram et al. | |
| 8,882,818 B1 | 11/2014 | Vestgaarden | |
| 8,945,135 B2 | 2/2015 | Ries et al. | |
| 9,009,012 B2 | 4/2015 | Bake et al. | |
| 9,216,089 B2 | 12/2015 | Major et al. | |
| 9,254,196 B2 | 2/2016 | Bake et al. | |
| 9,386,999 B2 | 7/2016 | Robertson et al. | |
| 9,826,993 B2 | 11/2017 | Bake et al. | |
| 2002/0095214 A1 | 7/2002 | Hyde | |
| 2002/0116006 A1 | 8/2002 | Cohen | |
| 2003/0018337 A1 | 1/2003 | Davis | |
| 2003/0100947 A1 | 5/2003 | Nadler et al. | |
| 2003/0144741 A1 | 7/2003 | King et al. | |
| 2003/0216669 A1 | 11/2003 | Lang et al. | |
| 2004/0098133 A1 | 5/2004 | Carignan et al. | |
| 2004/0147927 A1 | 7/2004 | Tsougarakis et al. | |
| 2004/0215203 A1 | 10/2004 | Michelson | |
| 2005/0209694 A1 | 9/2005 | Loeb | |
| 2005/0222575 A1 | 10/2005 | Ciccone et al. | |
| 2005/0234467 A1 | 10/2005 | Rains | |
| 2006/0198877 A1 | 9/2006 | Steinwachs et al. | |
| 2006/0206208 A1 | 9/2006 | Michelson | |
| 2006/0235539 A1 | 10/2006 | Blunn et al. | |
| 2006/0241594 A1 | 10/2006 | McCarthy et al. | |
| 2006/0247790 A1 | 11/2006 | McKay | |
| 2007/0021838 A1 | 1/2007 | Dugas et al. | |
| 2007/0100459 A1 | 5/2007 | Rhodes | |
| 2007/0159487 A1 | 7/2007 | Felt | |
| 2007/0233150 A1 | 10/2007 | Blain et al. | |
| 2007/0276501 A1* | 11/2007 | Betz | A61F 2/30942 623/17.16 |
| 2008/0051793 A1 | 2/2008 | Erickson et al. | |
| 2008/0243127 A1 | 10/2008 | Lang et al. | |
| 2008/0281328 A1 | 11/2008 | Lang et al. | |
| 2009/0209962 A1 | 8/2009 | Jamali | |
| 2009/0270868 A1 | 10/2009 | Park et al. | |
| 2009/0318927 A1 | 12/2009 | Martin et al. | |
| 2010/0185201 A1 | 7/2010 | Kim | |
| 2010/0234850 A1 | 9/2010 | Dees, Jr. et al. | |
| 2011/0029093 A1 | 2/2011 | Bojarski et al. | |
| 2011/0054483 A1 | 3/2011 | Howlett et al. | |
| 2011/0087332 A1* | 4/2011 | Bojarski | A61B 17/155 623/20.32 |
| 2011/0152869 A1 | 6/2011 | Ek et al. | |
| 2011/0166661 A1 | 7/2011 | Boileau et al. | |
| 2011/0238071 A1 | 9/2011 | Fernandez-Scoma | |
| 2012/0053588 A1 | 3/2012 | Lozier et al. | |
| 2012/0150030 A1 | 6/2012 | Reach, Jr. et al. | |
| 2012/0209394 A1 | 8/2012 | Bojarski et al. | |
| 2012/0271417 A1 | 10/2012 | Ek | |
| 2012/0316565 A1 | 12/2012 | Stark | |
| 2012/0330316 A1 | 12/2012 | Berelsman et al. | |
| 2012/0330317 A1 | 12/2012 | Berelsman et al. | |
| 2013/0165939 A1 | 6/2013 | Ries et al. | |
| 2013/0172891 A1 | 7/2013 | Bake et al. | |
| 2013/0173228 A1 | 7/2013 | Bake et al. | |
| 2013/0184820 A1 | 7/2013 | Schwartz et al. | |
| 2013/0185927 A1 | 7/2013 | Bake et al. | |
| 2013/0211410 A1 | 8/2013 | Landes et al. | |
| 2013/0211531 A1 | 8/2013 | Steines et al. | |
| 2014/0142643 A1 | 5/2014 | Bake et al. | |
| 2014/0208578 A1 | 7/2014 | Linderman et al. | |
| 2014/0224070 A1 | 8/2014 | Bake et al. | |
| 2014/0243836 A1 | 8/2014 | Bake et al. | |
| 2014/0249781 A1 | 9/2014 | Bake et al. | |
| 2014/0277522 A1 | 9/2014 | Goldberg et al. | |
| 2015/0190151 A1 | 7/2015 | Budhabhatti et al. | |
| 2015/0230874 A1* | 8/2015 | Musuvathy | A61B 19/50 703/1 |
| 2015/0320429 A1 | 11/2015 | Katrana et al. | |
| 2016/0089159 A1 | 3/2016 | Ardito et al. | |
| 2016/0100847 A1 | 4/2016 | Maxson | |
| 2016/0151076 A1 | 6/2016 | Bake et al. | |
| 2016/0199075 A1 | 7/2016 | Bake | |
| 2017/0100253 A1 | 4/2017 | Bake et al. | |
| 2017/0156890 A1 | 6/2017 | Bake et al. | |
| 2017/0172744 A1 | 6/2017 | Bake et al. | |

FOREIGN PATENT DOCUMENTS

| | | |
|---|---|---|
| EP | 1753365 B1 | 10/2007 |
| EP | 1864629 A2 | 12/2007 |
| EP | 2138110 A2 | 12/2009 |
| EP | 2389899 A1 | 11/2011 |
| EP | 2389905 A1 | 11/2011 |
| EP | 2389905 B1 | 5/2012 |
| EP | 2685905 | 1/2014 |
| JP | H8-502681 A | 3/1996 |
| JP | H10504217 A | 4/1998 |
| JP | 2008-539814 A | 11/2008 |
| WO | WO-94/09730 A1 | 5/1994 |
| WO | WO-96/24302 A1 | 8/1996 |
| WO | WO-2006/091686 A2 | 8/2006 |
| WO | WO-2007/014164 A2 | 2/2007 |
| WO | WO-2008/101090 A2 | 8/2008 |
| WO | WO-2008098061 A2 | 8/2008 |
| WO | WO-2008/138137 A1 | 11/2008 |
| WO | WO-2009/111626 A2 | 9/2009 |
| WO | WO-2009108591 A1 | 9/2009 |
| WO | WO-2010/099357 A1 | 9/2010 |
| WO | WO-2011/063257 A1 | 5/2011 |
| WO | WO-2012/027150 A2 | 3/2012 |
| WO | WO-2012/129018 A1 | 9/2012 |
| WO | WO-2012/143531 A1 | 10/2012 |
| WO | WO-2013/030371 A9 | 3/2013 |

OTHER PUBLICATIONS

Office Action dated May 13, 2015 issued in corresponding European patent application No. 12 755 990.4 (6 pages).
Notice of Rejection dated Feb. 19, 2018 issued in corresponding Japanese patent application No. 2017-500889 (2 pages) and its English-language translation thereof (3 pages).
Notification of Reasons for Refusal dated Mar. 29, 2018 issued in corresponding Japanese patent application No. 2017-500881 (4 pages) and English-language translation thereof (5 pages).
Notification of Reasons for Refusal dated Sep. 20, 2018 issued in Japanese patent application No. 2017-500889 (2 pages) and its English-language translation thereof (3 pages).

(56) References Cited

OTHER PUBLICATIONS

Extended European Search Report dated Dec. 17, 2018 in European Patent Application No. 18189755.4.
First Indian examination report dated Sep. 20, 2019 issued in Indian patent application No. 201717000875.

* cited by examiner

SURGICAL KIT FOR CARTILAGE REPAIR COMPRISING IMPLANT AND A SET OF TOOLS

CROSS-REFERENCE TO PRIOR APPLICATIONS

This application is a § 371 National Stage Application of PCT International Application No. PCT/EP2015/065781 filed Jul. 9, 2015, which claims priority to PCT/EP2014/064749 filed Jul. 9, 2014, each of which are herein incorporated by reference in their entirety.

FIELD OF EMBODIMENTS HEREIN

Embodiments relates in general to the field of orthopedic surgery and to cartilage and or bone resurfacing. Embodiments herein relates to an implant intended for replacing a part of a cartilage and or bone portion and to a design method for such an implant. Further embodiments also relates to surgery kits, kits of tools and a method for replacing a portion of an articular surface of a joint.

BACKGROUND

In the surgical operation of implanting such small implants it is critical that the implant is positioned in a precise manner. If the implant is offset from its intended position it may cause increased wear or load on the joint. For example, if the implant is tilted this may result in an edge that projects above the cartilage surface and causes wear on the opposing cartilage in the joint. Another example is when the implant is placed in a position with the surface of the implant projecting above the surface of the cartilage causing the joint to articulate in an uneven manner and increasing the load on an opposing point of the joint. For the patient, even small misplacements or deviations from an ideal position may result in pain, longer time for convalescence or even a surgical operation being done in vain and making it more difficult to repair the damage in the joint. A large burden is therefore placed on the surgeon not to misplace or misfit the implant.

PRIOR ART

Examples of prior art disclosing implants and tools for replacement of damaged cartilage are shown in:

EP 2 389 905 shows a design method for design of an implant and a tool kit.

WO2008098061 and US20120271417 disclose an implant for replacing a portion of an articular surface, wherein the implant comprises a first, second and third segment, wherein the first and the second segment partially overlap and the third and the second segment partially overlap. Implant is inserted by a guide system wherein reaming of the articulate surface is guided by using a guide pin. A drill guide may be used to establish the axes of the guide pin with respect to the articular surface.

U.S. Pat. No. 8,062,302 discloses a guide comprising a block having a patient-specific surface and first and second drilling holes.

US20110152869 discloses a trochlea repair system having two working axes displaced from each other, wherein the two working axes are used to create two partially overlapping sockets.

WO2010099357 discloses a system for repair of a defect in an articulate surface, comprising a guide block which may comprise an opening configured to allow the cutter to pass through the guide block.

OBJECT OF EMBODIMENTS HEREIN

The general object of embodiments herein is to solve the problem of providing a design method for an implant which enables precision in the insertion and positioning of the implant 1 at an articular surface of a joint. The object of embodiments herein is also to provide an implant.

There is a need for well fitting, customized implants as well as tools that are designed to guide and support the surgeon during the implant surgery.

Embodiments herein further seek to solve the partial problems of:

Providing a method for cartilage replacement wherein an implant is firmly attached in the joint and is well integrated into the surface structure of the joint, in order to generate optimal repair of damaged tissue and cause minimum damage to the surrounding tissue.

Providing an implant to be implanted in the joint, improving the positioning of the implant in order to generate optimal repair of damaged tissue and cause minimum damage to the surrounding tissue and aiding the surgeon in that positioning.

Providing a design method for designing an individually designed implant and or design of a guide for placement of such an implant.

By using the design method according to embodiments herein the surgeon can get a precise way to place an implant in the joint. The system according to embodiments herein wherein implant shapes may be built individually depending on cartilage damage and location of damage in the joint and by selecting from different sizes of circular shapes 303 or substantially circular shapes, partly overlapping each other in combinations which may be individually selected for one patient allows the surgeon to choose an implant which fits the size and shape of the bone and or cartilage damage or defect and gives the surgeon an easy to use design method and tool set for making the excisions needed.

The design method according to embodiments herein allows for producing an implant which is easy to fit to an individual damage and an individual patient. The design build up in this method, comprising choosing size, at least two circular shapes, implant thickness, implant surface shape, articular surface etc. for each implant, makes this solution unique and easy to individualize but still suitable for large scale industrial manufacturing. The circular shape building up of the implant makes the implant also easy to place by drilling and or reaming giving an exact fit of each implant in every patient.

SUMMARY

Embodiments herein relate to design methods for design of an individually customized implant, based on a 3D virtual model of an implant. The design method comprises identifying a damage area, presenting a virtual 3D view of the identified damage area, creating a 3D virtual implant comprising virtually placing in the 3D view a shape, wherein the area of the shape covers or partly covers the identified damage area, producing an implant based on the created 3D virtual implant.

In embodiments herein, the shape may comprise at least two circular shapes. Each circular shape may partly overlap at least one other circular shape, and the area of the circular shapes may cover or partly cover the identified damage area. The method may further comprise placing at least two points each from where an axis will origin from on the bone surface of the joint in or nearby the damage area or on a simulated bone surface which is a virtually created surface covering the damage area. The method may further comprise selecting an axe-distance, selecting diameter of circular shapes between 10-30 mm, or between 15-25 mm, selecting coverage of the implant area over the damage area. The coverage may be between 50-100%. The method may further comprise selecting angles of the axes which originates from a point of the simulated bone surface and have an angle of 0-40 degrees in relation to a bone-axis which extends in a normal direction in relation to a tangential plane of the simulated bone surface in that point. The method may further comprise selecting thickness of the implant by using the surfaces of the circular shapes placed on a simulated bone surface and extruding the area of the circular shapes to create a cylindrical body, outwards towards the virtual cartilage surface resulting in a simulated implant cartilage surface which is based on a simulated healthy cartilage surface in/of that particular area, and wherein the implant further optionally comprises at least one protruding peg.

In other embodiments, may each circular shape comprise a respective axis, and the overlap of the circular shapes may depends on selection of respective diameter of the respective circular shapes in combination with selection of a distance between an axis of one circular shape and another axis of another circular shape, and in combination with selection of a desired coverage for the implant of the damage area.

In other embodiments, may each circular shape comprise an axis and the overlap of the circular shapes may depend on selection of diameter between 1-3 cm of the circular shapes in combination with selecting an axe-distance of between 4 mm to 3 cm from one axis of one circular shape to another axis of another circular shape, and in combination with selection of 50-100% of coverage for the implant body over the damage area.

In other embodiments, may the identifying of a damage area in a patient be performed by taking CT, CBCT, MM images or the like of a joint of a patient, and using the images to create a 3D view of the bone and/or cartilage area and the bone and or cartilage damage using for example a software program useful for virtual 3D animation.

In other embodiments, may at least three circular shapes be placed partly overlapping, covering the damage area.

In other embodiments, may the circular shapes have a diameter between 0.5-4 cm.

In other embodiments, may at least 2-5 circular shapes be placed partly overlapping, covering the damage area.

In other embodiments, may virtually placing at least two circular shapes comprise virtually placing at least two points each from where an axis will origin from, wherein the points are placed on the bone surface of the joint in or nearby the damage area or the points are placed on a simulated bone surface which is a virtually created surface covering the damage area, wherein the simulated bone surface is a surface which preferably corresponds to a three dimensional, 3D, image of a bone surface in a healthy joint and wherein the points are in the center of the circular shapes, the circular shapes, partly overlapping each other, and wherein the axes are placed so that the combined area spread of the circular shapes covers or partly covers the identified damage area.

In other embodiments, may virtually placing at least two circular shapes be performed by placing the respective axes in a predetermined angle in relation to each other.

In other embodiments, may each circular shape have an axis which is 90° in relation to the surface of the circular shape.

In other embodiments, may the area of the placed circular shapes define the area which will comprise the created articulate surface of the implant.

In other embodiments, may the area of the placed circular shapes be a smaller area than the created articulate surface of the implant.

In other embodiments, may at least three circular shapes be virtually placed in a row or other symmetry wherein at least one circular shape overlaps with at least two other circular shapes.

In other embodiments, may each circular shape have an axis which is 90° in relation to the virtual bone contact surface of the created virtual implant.

In other embodiments, may the virtual implant bottom area of the combined circular shapes of the created implant be a planar surface.

In other embodiments, may creating a virtual model of an implant further comprise creating a simulated bone surface in the 3D view, which mimics a non-damaged bone surface in a healthy patient and using the simulated bone surface as a base when creating the virtual model of an implant.

In other embodiments, an implant designed according to any of the design methods herein is provided.

Embodiments herein is directed to a design method 2 for design of an individually customized implant 1 based on making a 3D computer plan of a virtual model of an implant wherein the design method comprises virtual digital representations of a position of the virtual model of the implant 42 in a virtual 3D view 9 of a joint of a patient, the design method 2 comprising steps;

A first damage identification step 101 comprising identifying a bone and or cartilage area 4 in a patient comprising a bone and or cartilage damage 5 and presentation of a 3D view 9 of the identified area using a software program A second virtual model making step 14 comprising making a 3D model of a virtual implant 42 comprising a step of virtually placing in the 3D view 9 at least two circular shapes 303, wherein each circular shape 303 partly overlaps at least one other circular shape 303', and wherein the combined area of the circular shapes 20 covers or partly covers the identified bone and or cartilage damage 5

A third production step 34 comprising producing an implant 1 which is conformed to mimic the volume and shape according to the created virtual model of the implant 42.

The design method 2 for designing of an individually customized implant 11 wherein the second virtual model making step 14 comprising making a 3D model of a virtual implant comprising a step of virtually placing in the 3D view 9 at least two circular shapes 303, wherein each circular shape 303 partly overlapping at least one other circular shape, and wherein the combined area of the circular shapes 20 covers or partly covers the identified bone and or cartilage damage 5 further comprising;

a first selection step comprising;
placing at least two points 19 each from where an axis 15 will origin from, the points 19 are placed on the bone surface 50 of the joint in or nearby the area of the bone and or cartilage damage 5 or the points 19 are placed on a simulated bone surface 51 which is a virtually created surface and covering the area of the bone and or cartilage damage 5 selecting axe-distance 53 selecting of diameter of circular shapes, the diameter 302 of the circular shapes 303 are selected between 10-30 mm or for example 15-25 mm selecting coverage of the implant area 7 over the cartilage and or bone damage 5, wherein the coverage may be between 50-100%.

and a second selection step comprising;

Selection of the angles 25 of the axes 15 and 15' which originates from a point 19 of the simulated bone surface 51 and wherein the axes 15 and 15' have and angle 25 of 0-40 degrees in relation to a bone-axis 60 which is normal in relation to a tangential plane 28 of the simulated bone surface in that point 19 and a third selection step comprising;

selection of thickness of the implant by using the surfaces of the circular shapes 303 placed on a simulated bone surface 51 and extruding the area of the circular shapes 303 to create a cylindrical body, outwards to the virtual cartilage surface resulting in a simulated implant cartilage surface 41 which is based on a simulated healthy cartilage surface 16 in/of that particular area and the implant further optionally comprises at least one protruding peg.

A design method 2 for design of an individually customized implant 1, wherein each circular shape 303 comprises an axis 15 and wherein the overlap 301 of the circular shapes 303 depends on selection of diameter 302 of the circular shapes 303 in combination of selection of closeness of an axis 15 of one circular shape 303 in relation to another axis 15' of another circular shape 303 in combination with selection of desired coverage for the implant of the bone and/or cartilage damage 5.

A design method 2 for design of an individually customized implant 1, wherein each circular shape 303 comprises an axis 15 and wherein the overlap 301 of the circular shapes 303 depends on selection of diameter 302 of between 1-3 cm of the circular shapes 303 in combination of selection axe-distance 53 of between 4 mm to 3 cm of one axis 15 of one circular shape 303 in relation to another axis 15' of another circular shape 303' in combination with selection of 50-100% of coverage for the implant body over the bone and/or cartilage damage 5.

A design method 2 for design of an individually customized implant, wherein identifying a cartilage and or bone area 4 in a patient is performed by taking CT, CBCT, MRI images or the like of a joint of a patient and using this images to create a 3D view 9 of the bone and or cartilage area 4 and the bone and or cartilage damage 5 using for example a software program useful for virtual 3D animation.

A design method 2 for design of an individually customized implant, wherein at least three circular shapes 303 is placed partly overlapping, covering the bone and or cartilage damage 5

A design method 2 for design of an individually customized implant 1, wherein the circular shapes 303 are in the size having a diameter of between 0.5-4 cm A design method 2 for design of an individually customized implant, wherein at least 2-5 circular shapes 303 are placed partly overlapping, covering the bone and or cartilage damage 5.

A design method 2 for design of an individually customized implant 1, wherein creating a virtual model of an implant 42 further comprises creating a simulated bone surface in the 3D view 9, which mimics a non-damaged bone surface in a healthy patient and using the simulated bone surface as a base when creating the virtual model of an implant.

A design method 2 for design of an individually customized implant 1 according to any of the preceding claims, wherein virtually placing at least two circular shapes 303 in the second step 14 in the method according to embodiments herein comprises virtually placing at least two points 19 each from where an axis 15 will origin from, the points 19 are placed on the bone surface 50 of the joint in or nearby the area of the cartilage and or bone damage 5 or the points 19 are placed on a simulated bone surface 51 which is a virtually created surface and covering the area of the cartilage and or bone damage 5 the simulated bone surface 51 is a surface which preferably corresponds to a three dimensional 3D image of a bone surface in a healthy joint and wherein the points 19 are in the center of the circular shapes 303, the circular shapes 303, partly overlapping each other, and wherein the axes 15 are placed so that the combined area spread 20 of the circular shapes 303 covers or partly covers the identified cartilage and or bone damage 5.

A design method 2 for design of an individually customized implant 1, wherein virtually placing at least two circular shapes 303 is performed by placing the virtual circular shapes 303 comprising axes 15 placed in a predetermined angle in relation to each other.

A design method 2 for design of an individually customized implant, wherein each circular shape has an axis which is 90° in relation to the surface of the circular shape 303.

A design method 2 for design of an individually customized implant, wherein the area of the placed circular shapes 303 defines the area which will comprise the created articulate surface 6 of the implant.

A design method 2 for design of an individually customized implant 1, wherein the area of the placed circular shapes 303 is a smaller area than the created articulate surface 6 of the implant.

A design method 2 for design of an individually customized implant 1, wherein virtually placing at least three circular shapes 303 in a row or other symmetry wherein at least one circular shape overlaps with at least two other circular shapes 303.

A design method 2 for design of an individually customized implant 1, virtually placing two circular shapes 303 wherein the circular shape overlaps each other.

A design method 2 for design of an individually customized implant 1, wherein each circular shape 303 has an axis 15 which is 90° in relation to the virtual bone contact surface of the created virtual implant 1

A design method 2 for design of an individually customized implant, wherein the virtual implant bottom area 38 of the combined circular shapes 303 of the created implant 1 is a planar surface.

An implant designed according to the design method 2 described above.

BRIEF DESCRIPTION OF THE FIGURES

Embodiments of embodiments herein will now be described in more detail with reference to the appended drawings. Please note that the exemplified embodiments of embodiments herein disclosed in the figures are not to be interpreted to limit the scope of embodiments herein.

FIG. 1 is an exemplified embodiment according to embodiments herein, not limiting of the scope of embodiments herein, disclosing a 3D view of a patient's knee joint comprising a cartilage damage, where the 3D view is created from MR data images or the like.

FIG. 8a is a view from one side and FIG. 8b is the virtual implant from above.

DETAILED DESCRIPTION OF EMBODIMENTS HEREIN

Introduction

Figure 1:
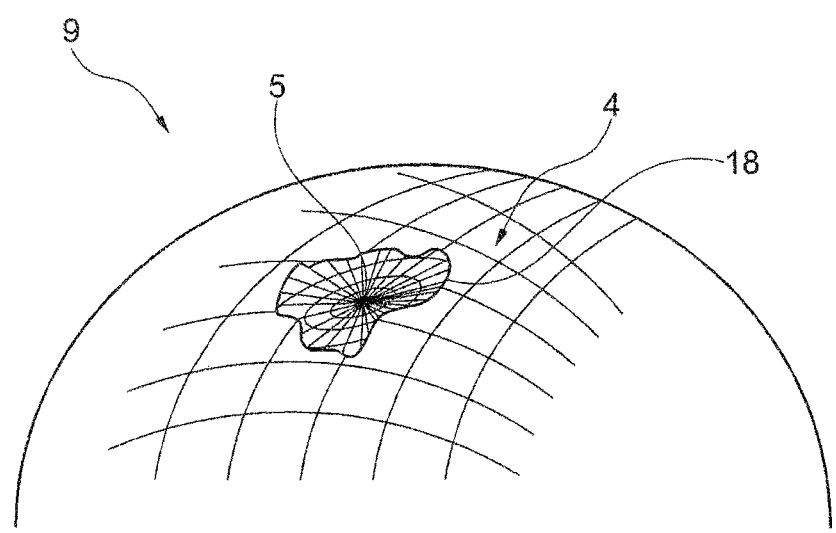

Embodiments herein relates to a design method 2 for design of an individually customized implant 1. The implant 1 designed by the method 2 according to embodiments herein is to be used for cartilage repair in a joint of a human or animal.

The design method 2 for design of an individually customized implant according to embodiments herein is described below.

Embodiments herein relate to design methods for design of an individually customized implant, based on a 3D virtual model of an implant. The design method comprises identifying a damage area, presenting a virtual 3D view of the identified damage area, creating a 3D virtual implant comprising virtually placing in the 3D view a shape, wherein the area of the shape covers or partly covers the identified damage area, producing an implant based on the created 3D virtual implant.

The design method 2 for design of an individually customized implant 1 according to embodiments herein is based on making a 3D computer plan of a virtual model of an implant 42 and wherein the design method comprises virtual digital representations of a position of the virtual model of the implant in a virtual 3D view 9 of a joint of a patient, the design method 2 comprising steps;

A first damage identification step 101 comprising identifying a bone and or cartilage area 4 in a patient comprising a bone and or cartilage damage 5 and presentation of a 3D view 9 of the identified area using a software program 31

A second virtual model making step 14 comprising making a 3D model of a virtual implant 42 comprising a step of virtually placing in the 3D view 9 at least two circular shapes 303, wherein each circular shape 303 partly overlaps at least one other circular shape 303', and wherein the combined area of the circular shapes 20 covers or partly covers the identified bone and or cartilage damage 5

A third production step 34 comprising producing an implant 1 which is conformed to mimic the volume and shape according to the created virtual model of the implant 42.

Figure 10:
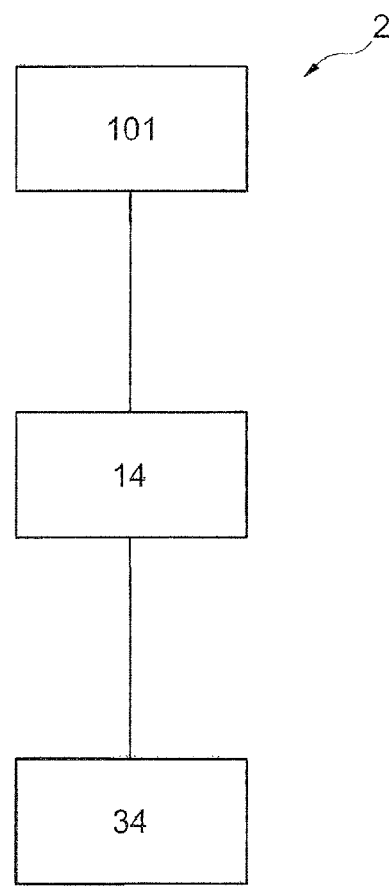
FIG. 10 is an exemplified embodiment according to embodiments herein, not limiting of the scope of embodiments herein, showing a design method according to embodiments herein comprising three general steps.

FIG. 10 shows the design method 2 according to embodiments herein comprising three general steps; A first damage identification step 101, a second virtual model making step 14, a third production step 34.

The design method according to embodiments herein allows for producing an implant which is easy to fit to repair an individual damage in a patient.

The design build up in this method comprising choosing size and at least two circular shapes and choosing overlap, implant thickness, articular surface etc. for each implant makes this solution unique and easy to individualize but still suitable for large scale industrial manufacturing. The circular shape build-up of the implant makes the implant also easy to place by drilling and or reaming giving an exact fit of each implant in every patient.

A First Damage Identification Step 101

A first damage identification step 101 comprises identifying a bone and or cartilage area 4 in a joint of a patient comprising a bone and or cartilage damage 5 and presentation of a 3D view 9 of the identified area using a software program. The first damage identification step 101 in the design method 2 according to embodiments herein is to identify the bone and or cartilage area 4 in a joint of a specific patient whom is in need of bone and or cartilage repair. This is done from 2D images such as MR images. A 3D view 9 of a joint comprising a bone and or cartilage area 4 and or comprising the bone and or cartilage damage 5 is created by taking images of the joint and converting them into a 3D view 9. The bone and or cartilage damage 5 can for example be identified in the 2D images which then are converted into a 3D view 9.

Useful imaging techniques are for example Computed Tomography CT, Cone Beam Computed Tomography CBCT, Magnetic resonance imaging MRI or other suitable techniques such as delayed Gadolinium-enhanced MRI of cartilage dGEMRIC techniques or the like. The taken 2D images of the joint are used to create a 3D model or view 9 of the patient's bone and or cartilage and using for example a software program, for example a CAD animation program for example a radiography software program or the like is useful for 3D animation.

A joint representation-CAD animation model is created which is a 3D view 9 comprising the bone and or cartilage area 4 based on images from the joint. This model is further comprising the bone and or cartilage damage 5.

A damage-representation CAD animation model which shows the bone and or cartilage damage 5 may be created manually from 2D images by manually marking out damaged area 45 pixels in each 2D image and from that create a 3D view 9 or the damage-representation CAD animation model may be a combination of the marked up 2D images.

In an automated process a computer program, for example a radiography software program, could be adapted to scan the images for predetermined characteristics of an area and or spread, curvature and or a location of bone and or cartilage damage 2 in the image data, and combine the automatically marked 2D images 47 into a 3D view 9 also called the damage representation CAD animation model. The size of the area which is of interest to map or to create a 3D view 9 of is usually not depending of the size of the cartilage damage and the type of joint or bone part which is to be repaired, usually the surgeon does not know where in the joint the damage is located before taking images of the patients joint, therefore usually, images of the whole bone and or cartilage area 4 of the joint are used to create a virtual 3D view 9. A virtual 3D view 9 is a joint representation CAD animation model which can be selected to show the bone and or cartilage area 4, the bone and or cartilage damage 5, placement of virtual implants etc.

In one embodiment according to embodiments herein a first damage identification step 101 of the design method 2 according to embodiments herein comprises identifying a bone and or cartilage area 4 in a patient by taking images of the injury or damage in the joint of a patient and then use these images of the individual patient's bone and or cartilage area 4 to create a joint representation CAD animation model.

See for example FIG. 1, not limiting for the scope of embodiments herein, for one view of a 3D view 9 of a patient's knee joint comprising a bone and or cartilage damage 5 which is created from MR images or the like. FIG. 1 shows a 3D view 9 of a patient's knee joint comprising a bone and or cartilage damage 5 wherein the borders around the bone and or cartilage damage 18 are marked-up.

Joints in a human or animal which may be repaired by the implant designed according to the design method 2 according to embodiments herein can be selected from for example any of a knee, hip, shoulder, toe or finger joint.

A Second Virtual Model Making Step 14

The second step 14 in the method according to embodiments herein comprises a first step of selecting a surface comprising at least two circular shapes which decides upon how large implant body is needed.

Figure 2:
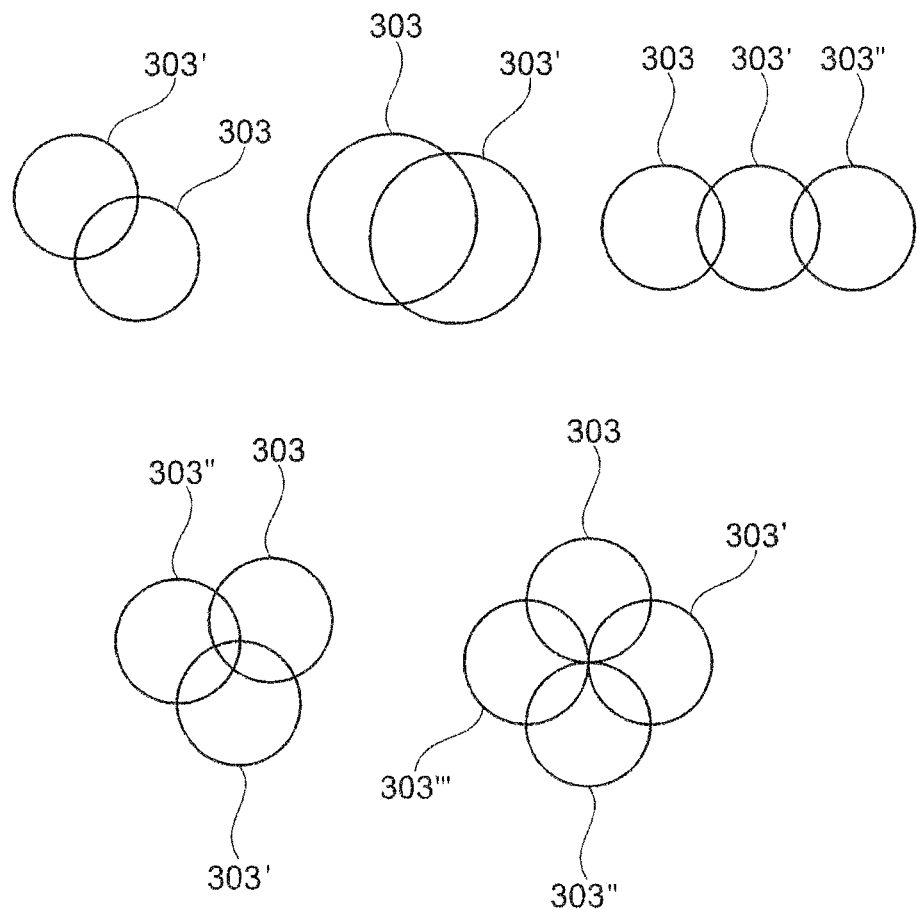
FIG. 2 is exemplified embodiments according to embodiments herein, not limiting of the scope of embodiments herein, showing different examples of placement of the circular shapes in the first step of the design method, in relation to each other.
Figure 11:
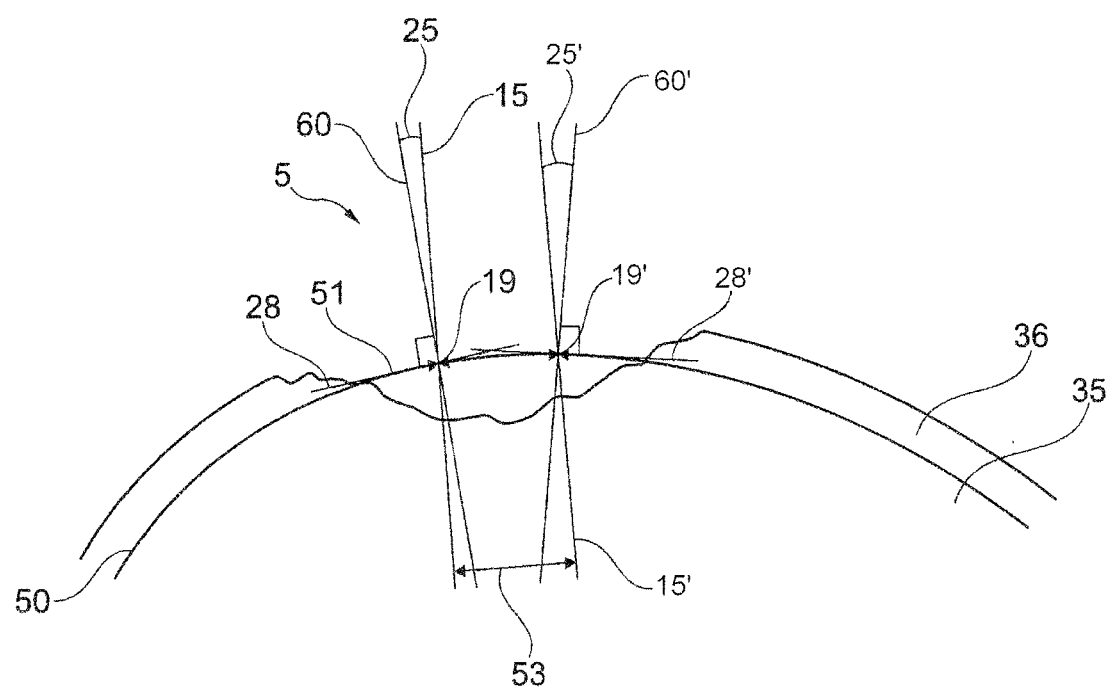
FIG. 11 is an exemplified embodiment according to embodiments herein, not limiting of the scope of embodiments herein, showing placement of axes of two circular shapes in a joint with a cartilage and bone damage, the placement of the axes is shown in relation to each other with an axe-distance and in relation to a simulated bone surface wherein the axes originates from a point of the simulated bone surface.
Figure 12:
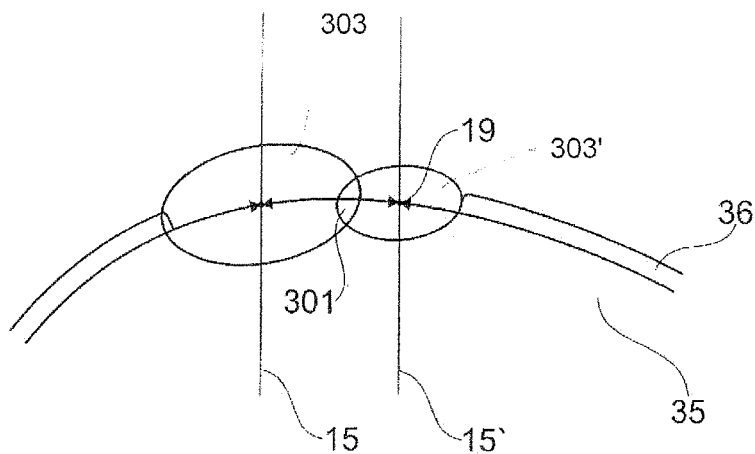
FIG. 12 shows the overlap 301 of the circular shapes 303 is in one embodiment of embodiments herein performed so that the diameter of the circular shapes 303 has an overlap 301 in relation to each overlapping circle.

In one embodiment, See FIG. 11 the second step 14 in the method according to embodiments herein comprises virtually placing at least two points 19 each from where an axis 15 will origin, the points 19 are placed on the bone surface 50 of the joint in or nearby the area of the bone and or cartilage damage 5 or the points 19 are placed on a simulated bone surface 51 which is a virtually created surface and covering the area of the bone and or cartilage damage 5. The simulated bone surface 51 is a surface which preferably corresponds to a three dimensional 3D image of a bone surface in a healthy joint. From FIG. 12 it can be seen that the points 19 are surrounded by selected circular shapes 303 and 303', the circular shapes 303 and 303' partly overlapping each other, and wherein the axes 15 and 15' are placed so that the combined area spread 301 of the circular shapes 303 covers or partly covers the identified bone and or cartilage damage 5. See FIG. 2 for examples on overlapping circular shapes 303 and 303'

The axes 15 are placed with a selected axe-distance 53 from each other.

Figure 5:
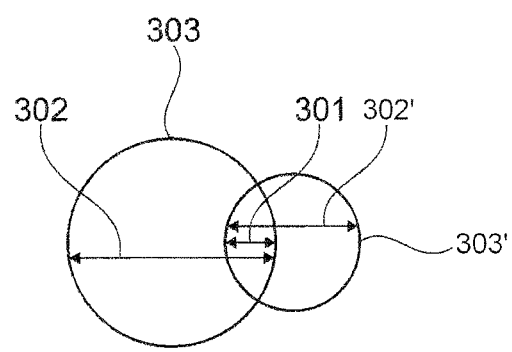
FIG. 5 is an exemplified embodiment according to embodiments herein, not limiting of the scope of embodiments herein, showing the 3D model of the patient's knee wherein the circular shapes have varying diameters.

In one embodiment of embodiments herein see FIG. 5 the second step 14 in the method according to embodiments herein comprises a first selection of diameters 302 of the circular shapes 303, selection of how much the circular shapes 303 should cover of the bone and or cartilage damage 5, selection of placement of axes 15 by selection of points 19 of intersection of the axes 15 on a simulated bone surface 51 or placement directly on a bone surface 50 in a 3D view of a joint.

Different types of selections may be comprised in the second virtual model making step 14 and are in one embodiment according to the design method 2 according to embodiments herein selected in the following order;

First selections;
  placing at least two points 19 each from where an axis 15 will origin from, the points 19 are placed on the bone surface 50 of the joint in or nearby the area of the bone and or cartilage damage 5 or the points 19 are placed on a simulated bone surface 51 which is a virtually created surface and covering the area of the bone and or cartilage damage 5
  selecting diameter of circular shapes, the diameters 302 of the circular shapes 303 are selected between 10-30 mm or for example 15-25 mm
  wherein the axe-distance 53 between the points 19 is for example between 6-32 mm or 7-20 mm Or 7-12 mm. The distance is the distance measured between the middle of each peg.
  selecting coverage of the implant area 20 over the cartilage and or bone damage 5. The coverage is preferably 100% but may be between 50-100%.
Second Selections;
  Selection of the angles 25 of the axes 15. Angles 25 in relation to simulated bone surface 51 or 50 and in relation to other axes.

Figure ii shows an exemplified embodiment according to embodiments herein, not limiting of the scope of embodiments herein, showing placement of axes of two circular shapes in a joint with a cartilage and bone damage, the placement of the axes 15 and 15' are shown in relation to each other with an axe-distance 53 and in relation to a simulated bone surface 51 wherein the axes 15 and 15' originate from a point 19 of the simulated bone surface 51 and wherein the axes 15 and 15' each has an angle 25 and 25' in relation to a bone-axis 60 and 60' which each is normal in relation to a tangential plane 28 and 28' of the simulated bone surface in the point 19 and 19'.

Third Selections;
Deciding the thickness and outer surface shape of the implant. Thickness of the implant is selected to be between 1-20 mm or for example or 2-15 mm
Creating a simulated cartilage surface 41 giving the surface of the virtual implant 42 based on information of a healthy cartilage surface of the specific patient.
the virtually created implant should preferably have at least a 1 mm thickness at the thinnest part or at least 2 mm thickness at the thinnest part of the implant.
In one embodiment the thickness of the implant is decided upon using the surfaces of the circular shapes 303 placed on a simulated bone surface 51 and extruding the area of the circular shapes 303 to create a cylindrical body, outwards to the virtual cartilage surface resulting in a simulated implant cartilage surface 41 which is based on a simulated healthy cartilage surface 16 in/of that particular area. The implant further optionally comprises at least one protruding peg.

Different Types of First and or Second and or Third Selections in Second Virtual Model Making Step 14 which May be Combined According to the Method of Embodiments Herein:

In one embodiment according to embodiments herein the axe-distance 53 is between 6-32 or for example 7-20 or for example 7-12 mm.

In one embodiment according to embodiments herein the axe-distance 53 is larger than 8 mm.

In one embodiment according to embodiments herein the axe-distance 53 is 8 mm.

The placements of the points 19 and/or axes 15 and/or the selection of diameters 302 of the circular shapes 303 are done manually by an operator using a software program or automatically by a software program 31.

Figure 6:
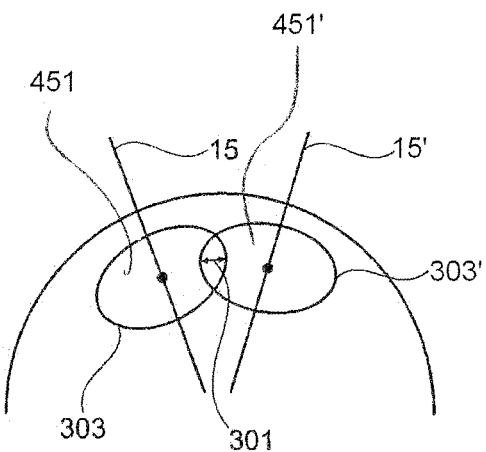
FIG. 6 is an exemplified embodiment according to embodiments herein, not limiting of the scope of embodiments herein, showing a view after placement of the circular shapes and design of circular shapes with non-parallel axes.

In one embodiment at least two axes 15 and 15' are parallel in relation to each other. In other embodiments the axes 15 and 15' have different angles in relation to each other and also in relation to a simulated bone surface 51. See for example FIG. 6 for an example according to embodiments herein wherein two circular shapes 303 and 303' are placed on a bone surface, with an overlap 301 and with non-parallel axes 15 and 15'. In FIG. 6 two surfaces 451 and 451' of a circular shape 303 and 303' are also shown.

In one embodiment the design method 2 for design of an individually customized implant comprises virtually placing at least two circular shapes 303 and 303' is performed by placing two circular shapes 303 and 303' so that the diameter of each circular shape 303 and 303' has a 20-90% or 40-70% overlap 301 in relation to the diameter of each circle The second virtual model making step 14 in the method according to one embodiment of embodiments herein comprises virtually placing at least two circular shapes 303 and 303', partly overlapping, covering or partly covering the identified bone and or cartilage damage 5.

Figure 7:
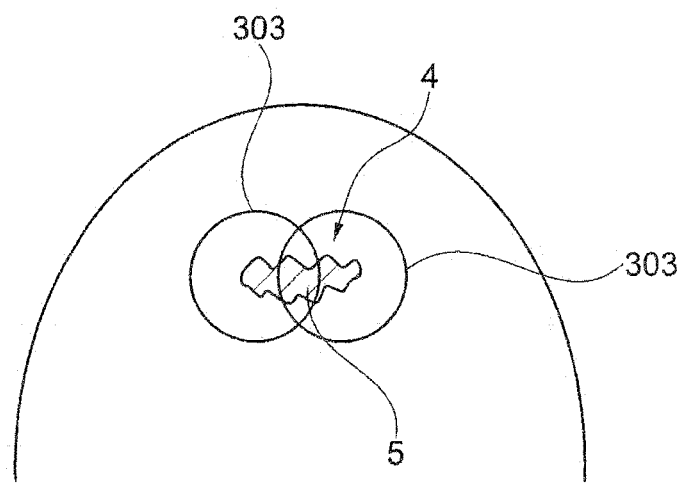
FIG. 7 is an exemplified embodiment according to embodiments herein, not limiting of the scope of embodiments herein, showing two circular shapes covering the bone and or cartilage damage.

FIG. 7 illustrates an example according to embodiments herein of the second virtual model making step 14 and comprises two virtually placed circular shapes 303 covering the identified cartilage and or bone damage 5 in a 3D view 9.

In one embodiment the second virtual model making step 14 in the design method 2 according to embodiments herein comprises;
virtually placing at least two circular shapes 303, partly overlapping, covering or partly covering the identified cartilage and or bone damage 5 and
virtually creating at least two directions of at least two circular shapes 303 in relation to the identified cartilage and or bone area 4.

In one embodiment of embodiments herein the different directions of the axes, for the angle of axis 15 and 15' are described. Axis 15 has an angle 25 of 0-40 degrees in relation to a bone-axis 60, which is normal in relation to an tangential plane 28 of the simulated bone surface 51 or in relation to the bone surface 51 in the point 19. Axis 15' has an angle 25' of 0-40 degrees in relation to a bone-axis 60' which is normal in relation to a tangential plane 28 of the simulated bone surface 51 in the point 19' in a 3D view 9 of a virtually repaired articulate surface according to embodiments herein.

In one embodiment the different axes 15 and 15' of the circular shapes 303 have directions that are parallel to each other. In one embodiment the different axes 15 and 15' of the circular shapes 303 have different directions in relation to each other.

In one embodiment, the second step 14 in the method according to embodiments herein comprises of virtually placing at least two circular shapes 303, partly overlapping, covering the identified bone and cartilage damage.

In one embodiment, the second step 14 in the method according to embodiments herein 2 comprises of virtually placing at least two circular shapes 303, partly overlapping, covering the identified bone and or cartilage damage 5 and wherein all the circular shapes 303 have identical or approximately the same diameter.

In one embodiment, the second virtual model making step 14 in the method according to embodiments herein comprises of virtually placing at least two circular shapes 303, partly overlapping, covering the identified bone and or cartilage damage 5 and wherein the different circular shapes 303 have diameters in varying sizes, for example one with smaller diameter than another. See for example FIG. 5 wherein one circular shape 303 has one diameter 302 and another circular shape 303' has a smaller diameter 302'.

In one embodiment the second virtual model making step 14 in the method according to embodiments herein comprises of virtually placing at least two circular shapes 303, partly overlapping, covering a part or covering the complete bone and or cartilage damage 5 identified in images 10 and presented in the 3D model of the bone and or cartilage area 4 in the joint identified in the first step 101 of the design method 2 according to embodiments herein.

The combined area 20 of the overlapping circular shapes 303 will together define the area 33 of the implant body 30 to be produced. In other words the area of the virtual implant body 30 means the sum of the spread of the shapes of the circular shapes 303. See FIG. 8b.

The placement of the circular shapes 303 in relation to each other may be placement in a row or in symmetric groups or for example in an asymmetric order. For different examples of placement patterns of the circular shapes 303 see FIG. 2.

The placement pattern is selected depending on for example the placement of the bone and or cartilage damage 5, and or the size of the bone and or cartilage damage 5 and or the spread of the bone and or cartilage damage 5 and or the depth of the bone and or cartilage damage 5.

The overlap 301 of the circular shapes 303 is in one embodiment of embodiments herein performed so that the diameter of the circular shapes 303 has a 20-90% overlap 301 or for example 30-80% or for example 40-70% in relation to the diameter 302 of each overlapping circle.

The overlap 301 of the circular shapes 303 is in one embodiment of embodiments herein performed so that the diameter of the circular shapes 303 has at least 40% overlap 301 in relation to the diameter of each overlapping circle.

The diameters of the circular shapes 303 and 303' according to embodiments herein are between 5-30 mm or between 10-25 mm or for example between 15-25 mm.

Figure 3:
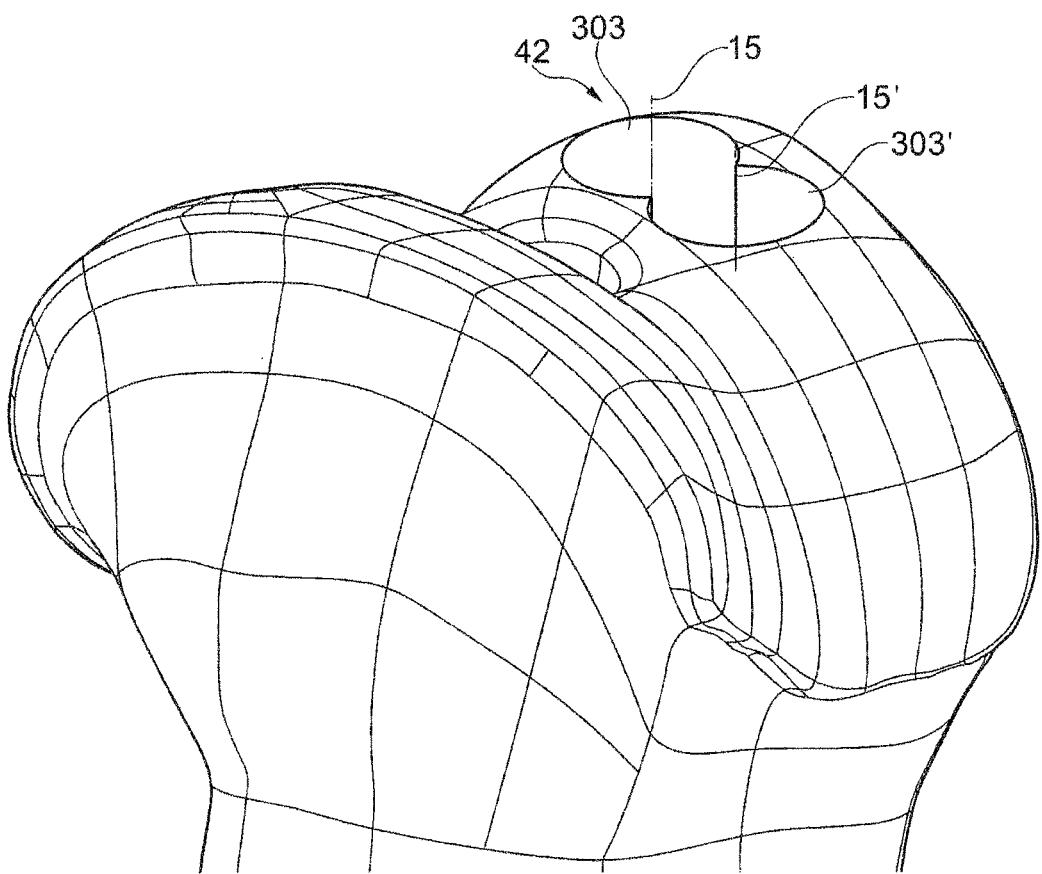
FIG. 3 is an exemplified embodiment according to embodiments herein, not limiting of the scope of embodiments herein, showing a virtual implant placed in a knee wherein the virtual implant comprises two circular shapes.

FIG. 3 shows one exemplified embodiment of embodiments herein. FIG. 3 shows a virtual implant 42 placed in a knee and wherein the virtual implant 42 comprises two circular shapes 303 and 303' placed so that they have an overlap.

Figure 8A:
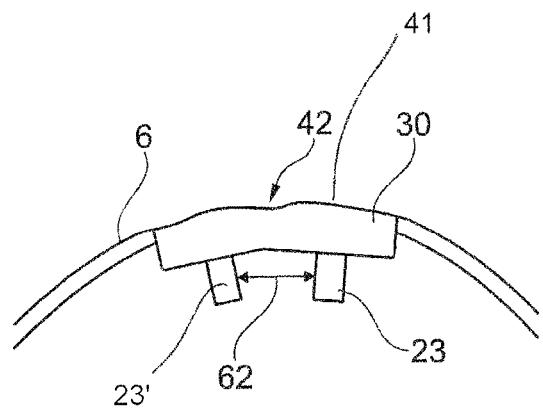
FIGS. 8a and 8b show an exemplified embodiment according to embodiments herein, not limiting of the scope of embodiments herein, showing the virtual model of the implant placed at the implantation site and comprising a simulated cartilage surface 6 of the implant 1 which simulates the cartilage surface before the cartilage damage.

FIGS. 8a and 8 show an exemplified embodiment according to embodiments herein, not limiting for the scope of embodiments herein, showing the virtual model of the implant 42 placed at the implantation site and comprising a simulated cartilage surface 41 of the virtual model of the implant 42 which mimics the cartilage surface before a cartilage damage. Further the virtual implant model 42 in the example in FIG. 8a comprises a virtual implant body 30 and two extending posts 23 and 23', see FIG. 8a.

Figure 8B:
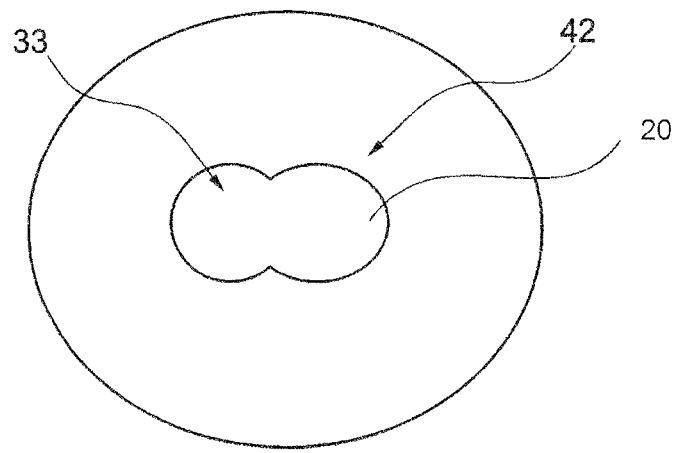

FIG. 8a is a view from one side and FIG. 8b is a view of a virtual model of the implant 42 from above and wherein the area 20 of the implant body 30 to be produced is shown.

Determination of Thickness.

When the axes 15 and 15' are determined and the circular shapes 303 placed in the 3D view 9, the side surfaces of the circular shapes 303 are created, leading to a cylindrical body with a patient specific outer top surface. The implant's side surface 29 should be extended from the circular shape 303. The implant further optionally comprises at least one protruding peg.

The virtually created implant should preferably have at least a 1 mm thickness at the thinnest part or at least 2 mm thickness at the thinnest part of the implant. The implant side surface is extruded from the circular shape 303 outwards to the cartilage surface ending with an implant simulated cartilage surface 41 which is based on a simulated healthy cartilage surface 16 in/of that particular area.

Figure 4:
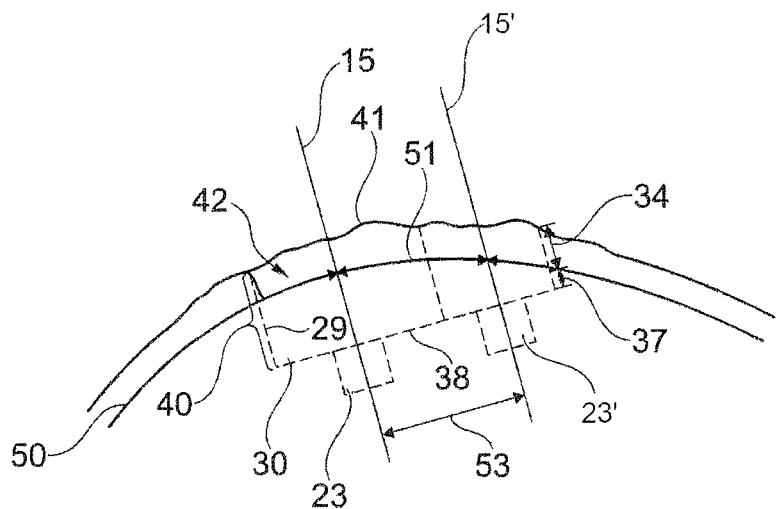
FIG. 4 is an exemplified embodiment according to embodiments herein, not limiting of the scope of embodiments herein, showing a view after placement of the circular shapes and design of circular shapes with parallel axes.

FIG. 4 shows one exemplified embodiment from the thickness determination step for the virtual model of the implant 42

FIG. 4 shows a 3D view 9 of a knee joint comprising a created simulated bone surface 51 wherein two points 19 are placed with a determined axe-distance 53. Surrounding both points 19 and placed on the simulated bone surface 51 are circular shapes 303 with a selected diameter 302, placed so that the circular shapes cover the bone and or cartilage damage. An angle of the axes is determined and then the thickness 40 of the implant body is determined by extending the circular shape wall of the virtual implant shape so that the thinnest point of the implant shape comprising the shortest lower wall 37 is at least 2 mm thick, and the upper wall of implant construction 39, is made as thick as the cartilage, and the implant surface is as thick as the surrounding cartilage so that the simulated cartilage surface 41 of virtual implant mimics a healthy cartilage in that area. The virtual implant bottom area 38 is a planar area in this example and may further comprise protruding extending posts 23.

In one embodiment the virtual implant body 30 has a thickness of between 1-30 mm or between 2-20 mm or between 2-10 mm or thicker than 2 mm.

By using a simulated bone surface 51 the base for building the virtual implant model 42 according to embodiments herein is more accurate than using image information of the cartilage. A more precise and more exact customized virtual implant 42 is achieved when the implant appearance is based on bone surface image data and building the virtual implant 42 from that data.

By creating a 3D computer plan of the implant according to embodiments herein, design parameters for a medical implant are generated as described above. The 3D computer plan may also comprise further steps for example a step which includes generating a length and a cross-section profile for an extending post 23 extending from a bone contacting surface of the implant, dependent on predetermined rules related to the size and shape of the cartilage damage. The size and shape of the extending post is selected automatically according to a predetermined scheme or is selected manually by an operator.

An extending post may have a diameter of 2-7 mm or for example between 4-5 mm and a length of between 3-20 mm or for example 13-17 mm.

In one embodiment according to embodiments herein the 3D computer plan may also comprise a step which includes generating a length and cross-section profile or diameter for at least one extending post 23 extending from the virtual implant bottom area 38 of the virtual implant 42 dependent on predetermined rules related to the size and shape of the bone and or cartilage damage.

In one embodiment according to embodiments herein the 3D computer plan may also comprise a step which includes generating length and cross-section profile for at least one extending post 23 extending from the virtual implant bottom area 38 of the virtual implant 42 and wherein at least one extending post 23 has a slightly larger diameter than at least another extending post 23.

In one embodiment according to embodiments herein the 3D computer plan may also comprise a step which includes generating a length and cross-section profile for at least one extending post 23 extending from the virtual implant bottom area 38 of the virtual implant 42 and wherein at least one extending post is designed to achieve press fit at the recess at the bone site prepared for receiving the extending post and at least one extending post which is smaller than the recess at the bone site prepared for receiving the extending post 23.

In one embodiment according to embodiments herein the 3D computer plan may also comprise a step which includes generating a length of a first extending post 23 which is longer the length of the other extending posts 23. It is also possible to generate a first extending post without generating a second extending post. Thus only one extending post 23 is needed.

By making an implant according to one embodiment of embodiments herein with at least two extending posts 23 and wherein only one extending post 23 is designed to achieve press fit when the implant is inserted in the bone an implant is formed which is easy to place and which is less sensitive to the precision of the drill holes when one extending post actually achieves the correct placement and fastening and the other drill hole and the other extending post is present for guiding. This also makes the implant 1 less prone to have tensions when placed in the implantation site.

There is still a further advantage if only one peg is formed, which gives even less tensions at the implant site.

In one embodiment the extending pots 23 has similar or identical diameter.

In one embodiment according to embodiments herein the virtual implant bottom area construction 38 is a planar surface. The virtual implant bottom area 38 is the area of the implant facing the bone when the implant is inserted in a joint and has the spread of the combined overlapping circular shapes 303.

In one embodiment according to embodiments herein the implant bottom area construction 38 has a protruding edge 47.

Figure 13:
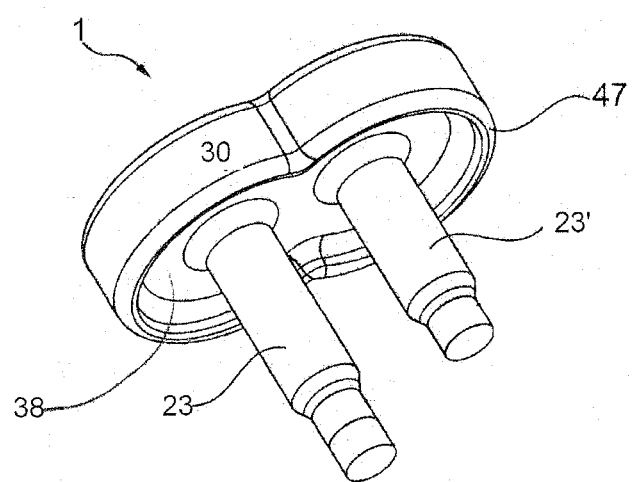
FIG. 13 shows an implant comprising two extending posts according to embodiments herein.

FIG. 13 shows an exemplified embodiment of an implant 1 according to embodiments herein. Having two circular shapes, having two extending posts 23 and 23' or pegs and a protruding edge 47 surrounding the implant body 30.

Figure 9:
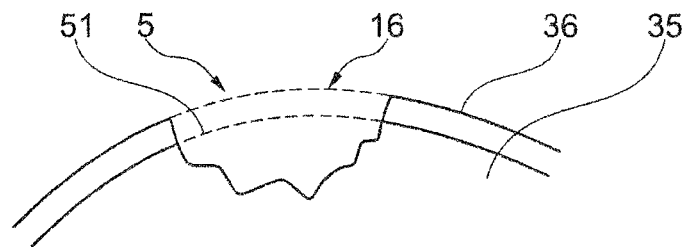
FIG. 9 is an exemplified embodiment according to embodiments herein, not limiting of the scope of embodiments herein, showing a bone and cartilage damage wherein a simulated repair surface 16 is created which is a surface which preferably corresponds to a three dimensional 3D image of a simulated healthy cartilage surface

FIG. 9 is an exemplified embodiment according to embodiments herein, not limiting for the scope of embodiments herein and shows a cartilage and bone damage 5 wherein a simulated repair surface is created 16 simulating a healthy cartilage surface. In the FIG. 9 bone 35 and cartilage 36 of the joint are also present. The figure shows a simulated cartilage surface 16 and a simulated healthy bone surface 51 which are based on a simulated healthy cartilage and or bone surfaces in/of that particular area.

A Third Production Step 34

The design method according to embodiments herein involves a third production step 34 of producing an implant 1 comprising an articular surface 6 which is designed to have a spread that is conformed to mimic the area formed by the virtually placed circular shapes 303.

The third production step 34 according to embodiments herein comprises producing an implant 1 having the shape and volume as the virtual implant 42 planned and created in first damage identification step 101 and the second virtual model making step 14.

The implant according to embodiments herein is produced in a biocompatible metal, metal alloy, ceramic or polymeric material. More specifically it can comprise any metal or metal alloy used for structural applications in the human or animal body, such as stainless steel, cobalt-based alloys, chrome-based alloys, titanium-based alloys, pure titanium, zirconium-based alloys, tantalum, niobium and precious metals and their alloys. If a ceramic is used as the biocompatible material, it can be a biocompatible ceramic such as aluminium oxide, silicon nitride or yttria-stabilized zirconia. Preferably the articulate surface comprises a cobalt chrome alloy CoCr or stainless steel, diamond-like carbon or a ceramic. The articulate surface 6 and the core of the implant body 3 may comprise the same or different materials.

The articulate surface 6 of the implant 1 may also be further surface treated in order to e.g. achieve an even more durable surface or a surface with a lower friction coefficient. Such treatments may include, for example, polishing, heat treatment, precipitation hardening or depositing a suitable surface coating.

The implant bottom area 38 is configured to face or contact the bone structure of the joint. In one embodiment the implant bottom area 38 comprises a biocompatible metal, metal alloy or ceramic, such as any of the metals, metal alloys or ceramic described above for the articulate surface 6. Preferably it comprises a cobalt chrome alloy CoCr, a titanium alloy, titanium or stainless steel.

In one embodiment the implant bottom area 38 comprises, or in one specific embodiment is coated with, a bioactive material or a material that promotes osseointegration and or bone growth. In an alternative embodiment of embodiments herein the bone contact surface does not comprise such a material and/or is uncoated.

The material that promotes osseointegration and or bone growth of the bone contact surface, if present, preferably stimulates bone to grow into or onto the implant surface. Several materials that have a stimulating effect on bone growth are known and have been used to promote adherence between implants and bone. Examples of such prior art materials include bioactive glass, bioactive ceramics and biomolecules such as collagens, fibronectin, osteonectin and various growth factors. A commonly used material in the field of implant technology is the ceramic hydroxyapatite HA, chemical formula $Ca_{10}PO_{46}OH_2$. HA is the major mineral constituent of bone and is able to slowly bond with bone in vivo. Another material commonly used in prior art is bioactive glass. Bioactive glasses, generally comprising $SiO_2$, $CaSiO_3$, $P_2O_5$, $Na_2O$ and/or $CaO$ and possibly other metal oxides or fluorides, are able to stimulate bone growth faster than HA.

The materials described above have an anabolic effect on the bone i.e. stimulates bone growth. The fixation of the implant can also be improved by decreasing the catabolic processes i.e. decrease the amount of bone resorption next to the implant. The bone contact surface 21 and/or the extending post can also be modified with bisphosphonates.

The software program wherein the second step according to the design method of embodiments herein is performed can in this third production step 34 be connected to manufacturing devices, for example a laser printer, a lathe and/or a reamer, and the parts of the kit are manufactured using e.g. additive manufacturing, laser sintering techniques, turnery or reaming.

The articulate surface 6 of the implant 1 designed using the design method according to embodiments herein is created by simulating a surface, mimicking a non-damaged cartilage surface in that specific site in a healthy patient or is created by creating a 3D surface based on the individual 3D damage and manually create a simulated surface above the cartilage damage wherein a part of the surface is identical to the patient's surface and a part is a simulation of a surface covering the actual damage.

The invention claimed is:

1. A design method for design of an individually customized implant for bone or cartilage resurfacing, based on a 3D virtual model of the implant, the design method comprising:
   identifying a damage area of a joint by taking computed tomography (CT), cone beam computed tomography (CBCT), or magnetic resonance imaging (MRI) images of the joint;
   presenting a virtual 3D view of said identified damage area;
   placing in said virtual 3D view at least two overlapping substantially circular shapes so that the combined area of the overlapping substantially circular shapes covers or partly covers said identified damage area, said placing comprising:
      placing at least two points each from where an axis will originate from on the bone surface of the joint in or nearby the damage area or on a simulated bone surface which is a virtually created surface covering the damage area;
      selecting axes-distance;
      selecting diameters of substantially circular shapes between 10-30 mm;
      selecting coverage of the implant area over the damage area, wherein the coverage is between 50-100%; and
      selecting angles of the axes and each of which originates from a point of said simulated bone surface and has an angle of 0-40 degrees in relation to a bone-axis which extends in a normal direction in relation to a tangential plane of the simulated bone surface in that point;
   selecting thickness of the implant by using the surfaces of the substantially circular shapes placed on a simulated bone surface and extruding the area of the substantially circular shapes to create a cylindrical body, outwards towards the virtual cartilage surface resulting in a simulated implant cartilage surface which is based on a simulated healthy cartilage surface in/of that particular area, and wherein the implant further optionally comprises at least one protruding peg;

creating a simulated repair surface which is individually customized in mimicking a non-damaged cartilage surface of the joint for which said damage area was identified; and creating a 3D virtual implant from the placement of the at least two overlapping substantially circular shapes and the simulated repair surface.

2. The design method according to claim 1, further comprising creating a 3D view of the bone, cartilage area, cartilage damage, or a combination thereof based on the CT, CBCT or MRI images of the joint.

3. The design method according to claim 1, wherein each substantially circular shape comprises a respective axis, and wherein the overlap of the substantially circular shapes depends on selection of respective diameter of the respective substantially circular shapes in combination with selection of a distance between an axis of one substantially circular shape and another axis of another substantially circular shape, and in combination with selection of a desired coverage for the implant of the damage area.

4. The design method according to claim 1, wherein each substantially circular shape comprises an axis and wherein the overlap of the substantially circular shapes depends on selection of diameters between 1-3 cm of the substantially circular shapes in combination with selecting an axes-distance of between 4 mm to 3 cm from one axis of one substantially circular shape to another axis of another substantially circular shape, and in combination with selection of 50-100% of coverage for the implant body over the damage area.

5. The design method according to claim 1, wherein at least three substantially circular shapes are placed partly overlapping, covering said damage area.

6. The design method according to claim 1, wherein said substantially circular shapes have a diameter between 0.5-4 cm.

7. The design method according to claim 1, wherein at least 2-5 substantially circular shapes are placed partly overlapping, covering said damage area.

8. The design method according to claim 1, wherein virtually placing at least two substantially circular shapes comprises virtually placing at least two points each from where an axis will originate from, wherein the points are placed on the bone surface of the joint in or nearby the damage area or the points are placed on a simulated bone surface which is a virtually created surface covering the damage area, wherein said simulated bone surface is a surface which preferably corresponds to a three dimensional (3D) image of a bone surface in a healthy joint and wherein the points are in the center of the substantially circular shapes, the substantially circular shapes, partly overlapping each other, and wherein the axes are placed so that the combined area spread of the substantially circular shapes covers or partly covers said identified damage area.

9. The design method according to claim 1, wherein virtually placing at least two substantially circular shapes is performed by placing the respective axes at a predetermined angle in relation to each other.

10. The design method according to claim 1, wherein each substantially circular shape has an axis which is 90° in relation to the surface of the substantially circular shape.

11. The design method according to claim 1, wherein the area of the placed substantially circular shapes defines the area which will comprise the created articulate surface of the implant.

12. The design method according to claim 3, wherein the area of the placed substantially circular shapes is a smaller area than the created articulate surface of the implant.

13. The design method according to claim 1, wherein virtually placing at least three substantially circular shapes in a row or other symmetry wherein at least one substantially circular shape overlaps with at least two other substantially circular shapes.

14. The design method according to claim 1, wherein each substantially circular shape has an axis which is 90° in relation to the virtual bone contact surface of the created virtual implant.

15. The design method according to claim 1, wherein the virtual implant bottom area of the combined substantially circular shapes of the created implant is a planar surface.

16. The design method according to claim 1, wherein creating a virtual model of an implant further comprises creating a simulated bone surface in the 3D view, which mimics a non-damaged bone surface in a healthy patient and using said simulated bone surface as a base when creating the virtual model of an implant.

17. An implant designed according to the design method in claim 1.

18. The design method according to claim 1, further comprising producing instructions for making an implant based on said created 3D virtual implant.

* * * * *